United States Patent
Yoshikawa et al.

(10) Patent No.: US 8,071,633 B2
(45) Date of Patent: Dec. 6, 2011

(54) **PHARMACEUTICAL COMPOSITION FOR TREATING *SPINOCEREBELLAR ATAXIA***

(75) Inventors: Takayoshi Yoshikawa, Osaka (JP); Goro Katsuura, Osaka (JP)

(73) Assignee: Shionogi & Co., Ltd., Osaka-Shi (JP)

( * ) Notice: Subject to any disclaimer, the term of this patent is extended or adjusted under 35 U.S.C. 154(b) by 929 days.

(21) Appl. No.: 11/662,182

(22) PCT Filed: Sep. 8, 2005

(86) PCT No.: PCT/JP2005/016994
§ 371 (c)(1),
(2), (4) Date: Apr. 9, 2007

(87) PCT Pub. No.: WO2006/028277
PCT Pub. Date: Mar. 16, 2007

(65) Prior Publication Data
US 2008/0027116 A1    Jan. 31, 2008

Related U.S. Application Data

(60) Provisional application No. 60/613,717, filed on Sep. 29, 2004.

(30) Foreign Application Priority Data

Sep. 9, 2004   (JP) ................. 2004-261977

(51) Int. Cl.
  *A61K 31/425*  (2006.01)
  *A61K 38/00*  (2006.01)
  *A61K 38/06*  (2006.01)
(52) U.S. Cl. ...... 514/365; 514/17.7; 514/18.2; 514/21.9
(58) Field of Classification Search .................. 514/365, 514/19
  See application file for complete search history.

(56) References Cited

U.S. PATENT DOCUMENTS 5,151,497 A    9/1992    Uchida et al.
(Continued)

FOREIGN PATENT DOCUMENTS

EA    0 933 379 A1    8/1999
(Continued)

OTHER PUBLICATIONS

Kinoshita et al. "Taltirelin Hydrate (TA-0910): An orally active thyrotropin-releasing hormone mimetic agent with multiple actions," CNS Drug Reviews, 1998, vol. 4, No. 1, pp. 25-41.*

(Continued)

*Primary Examiner* — Shengjun Wang
(74) *Attorney, Agent, or Firm* — Birch, Stewart, Kolasch & Birch, LLP

(57) ABSTRACT

This invention provide to a pharmaceutical composition for treating spinocerebellar ataxia (or atrophy, degeneration) or multiple system atrophy, or for improving ataxia or equilibrium disturbance comprising a compound of the formula (I):

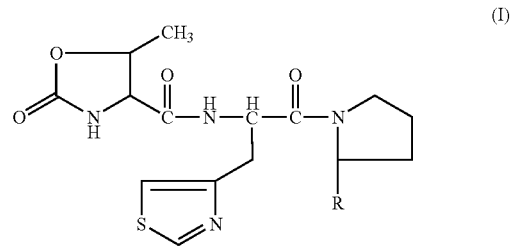

wherein R is methyl, cyano or carbamoyl, a pharmaceutically acceptable salt, or a solvate thereof as an active ingredient.

7 Claims, 2 Drawing Sheets

U.S. PATENT DOCUMENTS

| | | | |
|---|---|---|---|
| 5,686,420 A | * | 11/1997 | Faden .......................... 514/18 |
| 6,319,902 B1 | | 11/2001 | Sugawara et al. |
| 7,129,256 B2 | | 10/2006 | Shinohaea et al. |

FOREIGN PATENT DOCUMENTS

| | | |
|---|---|---|
| EP | 0 384 380 A2 | 8/1990 |
| EP | 1084704 A1 | 3/2001 |
| EP | 1300155 A1 | 4/2003 |
| EP | 1 321 151 A1 | 6/2003 |
| JP | 59-155346 A | 9/1984 |
| JP | 60-190795 A | 9/1985 |
| JP | 61-033197 A | 2/1986 |
| JP | 63-290876 A | 11/1988 |
| JP | 09-157286 A | 6/1997 |
| WO | WO-99/53941 A1 | 10/1999 |

OTHER PUBLICATIONS

The Merck Munal, Fifteenth Edition, 1987, pp. 1421-1423.*

Miyamoto et al., "Effects of a sustained release formulation of thyrotropin-releasing hormone on behavioral abnormalities in senescence-accelerated mice", European Journal of Pharmacology, vol. 271, pp. 357-366, 1994.

Asu no Shinyaku 2004, 409.

Nanzando's Medical Dictionary (1990.2.1, Ver. 17, pp. 235, 1085, and 1122).

* cited by examiner

PHARMACEUTICAL COMPOSITION FOR TREATING *SPINOCEREBELLAR ATAXIA*

TECHNICAL FIELD

The present invention relates to a pharmaceutical composition for treating spinocerebellar ataxia (or atrophy, degeneration) or multiple system atrophy, or for improving ataxia or equilibrium disturbance.

BACKGROUND ART

Spinocerebellar ataxia (SCA) includes neurodegeneration diseases in which the main locus of pathological change exists in nucleus or neural pathway of cerebellum, brainstem or spinal cord. As a main physical change of SCA, cerebellar ataxia or posterior column ataxia is shown. SCA is classified into hereditary diseases such as hereditary olivo-ponto-cerebellar atrophy, hereditary cortical cerebellar atrophy, Machado-Joseph disease, Friedreich's ataxia, hereditary Dentatorubral pallidoluysian atrophy and the like, and non-heritable diseases such as olivo-ponto-cerebellar atrophy, Shy-Drager syndrome, striato-nigral degeneration, cortical cerebellar atrophy and the like, and critical causes of these diseases have been unknown. Although conditions of diseases and progresses of the condition depend on type of diseases, all of diseases are progressive. The patients are finally confined to their beds and often lead to pulmonitis, asphyxia or sudden death. SCA is neural intractable diseases of unknown causes and investigations of the causes and establishment of an effective method for the treatment have been required.

Because striato-nigral degeneration, olivo-ponto-cerebellar atrophy and Shy-Drager syndrome have many common features in pathological, findings, they can be classified as multiple system atrophy. A definition for classification between spinocerebellar ataxia and multiple system atrophy are indefinite.

Thyrotropin-releasing hormone (TRH) is considered to be effective for treating or amelioration of spinocerebellar ataxia, and the compounds described in Patent Literature 1 and Non-Patent Literature 1 are used for a pharmaceutical composition for treating spinocerebellar ataxia. In Patent Literatures 2 to 7 and Non-Patent Literature 2, it is described that compounds having TRH-like activity are effective for treating spinocerebellar ataxia and TRH derivatives have been developed as a drug for spinocerebellar ataxia. A more excellent pharmaceutical composition for treating and ameliorating spinocerebellar ataxia has been desired.

Patent Literature 8 discloses compounds which show activating effect of central nervous system and which are useful for treating various symptoms caused by hypoactivity of dopamine system, norepinephrine system and acetylcholine system. The chemical structures of the compounds of the present invention are disclosed.

Patent Literature 9 discloses that the compounds of the present invention are useful for treating Parkinson's diseases, and Patent Literature 10 discloses that bioavailability (hereinafter referred to as BA) of the compounds are 4 to 34 times higher than that of TRH or TRH derivatives.

None of the prior art discloses that the compounds of the present invention have particular effect for treating spinocerebellar ataxia or multiple system atrophy.

| | |
|---|---|
| Patent Literature 1 | JP 61-33197 A |
| Patent Literature 2 | JP 63-290876 A |
| Patent Literature 3 | JP3-236397 A |
| Patent Literature 4 | JP 6-56886 A |
| Patent Literature 5 | JP 9-157286 A |
| Patent Literature 6 | JP 59-155346 A |
| Patent Literature 7 | JP 60-190795 A |
| Patent Literature 8 | WO98/08867 |
| Patent Literature 9 | WO02/17954 |
| Patent Literature 10 | WO99/53941 |
| Non-Patent Literature 1 | European Journal of Pharmacology, 1994, vol. 271, p. 357 |
| Non-Patent Literature 2 | "Asu no Shinyaku, Division of drug efficacy, drugs for neurosystem and sensory organ-2, drugs for central nervous system, (vol. 2), drugs for peripheral nervous system", Technomics, Inc, published on Jul. 22, 2004, page 409 |

DISCLOSURE OF INVENTION

The present invention provides a pharmaceutical composition for treating spinocerebellar ataxia (atrophy or degeneration) or multiple system atrophy, or for improving ataxia or equilibrium disturbance.

The present invention provides (1) A pharmaceutical composition for treating spinocerebellar ataxia or multiple system atrophy comprising a compound of the formula (I):

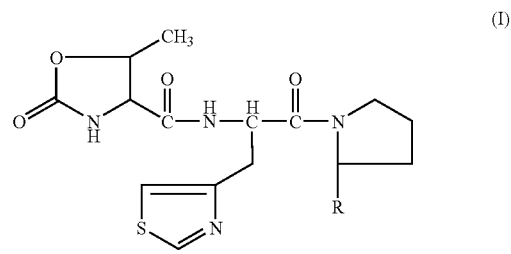

wherein R is methyl, cyano or carbamoyl, a pharmaceutically acceptable salt, or a solvate thereof as an active ingredient.

(2) A pharmaceutical composition for improving ataxia comprising a compound of the formula (I) as described in the above (1), a pharmaceutical acceptable salt, or a solvate thereof as an active ingredient.

(3) A pharmaceutical composition for improving equilibrium disturbance comprising a compound of the formula (I) as described in the above (1), a pharmaceutical acceptable salt, or a solvate thereof as an active ingredient.

(4) The composition as described in the above (1) wherein spinocerebellar ataxia or multiple system atrophy is olivo-ponto-cerebellar atrophy or striato-nigral degeneration.

(5) The composition as described in one of the above (1) to (4) wherein R is methyl.

(6) The composition as described in the above (5) wherein the compound of the formula (I) is monohydrate or trihydrate.

(7) Use of a compound of the formula (I) as described in the above (1), a pharmaceutically acceptable salt, or a solvate thereof for the preparation of a medicament for treating spinocerebellar ataxia.

(8) Use of a compound of the formula (I) as described in the above (1), a pharmaceutically acceptable salt, or a solvate thereof for the preparation of a medicament for improving ataxia.

(9) Use of a compound of the formula (I) as described in the above (1), a pharmaceutically acceptable salt, or a solvate thereof for the preparation of a medicament for improving equilibrium disturbance.

(10) Method for treating spinocerebellar atrophy or multiple system atrophy, or for improving ataxia or equilibrium disturbance comprising administering a therapeutically effective amount of a compound of the formula (I) as described in the above (1), a pharmaceutically acceptable salt or a solvate thereof, to a mammal in need thereof.

Effect of the Invention

The compounds of the present invention have an effect for improving ataxia or equilibrium disturbance caused by spinocerebellarataxia or multiple system atrophy, and are useful for a composition for treating spinocerebellar ataxia or multiple system atrophy, or for improving ataxia or equilibrium disturbance.

BEST MODE FOR CARRYING OUT THE INVENTION

Figure 1:
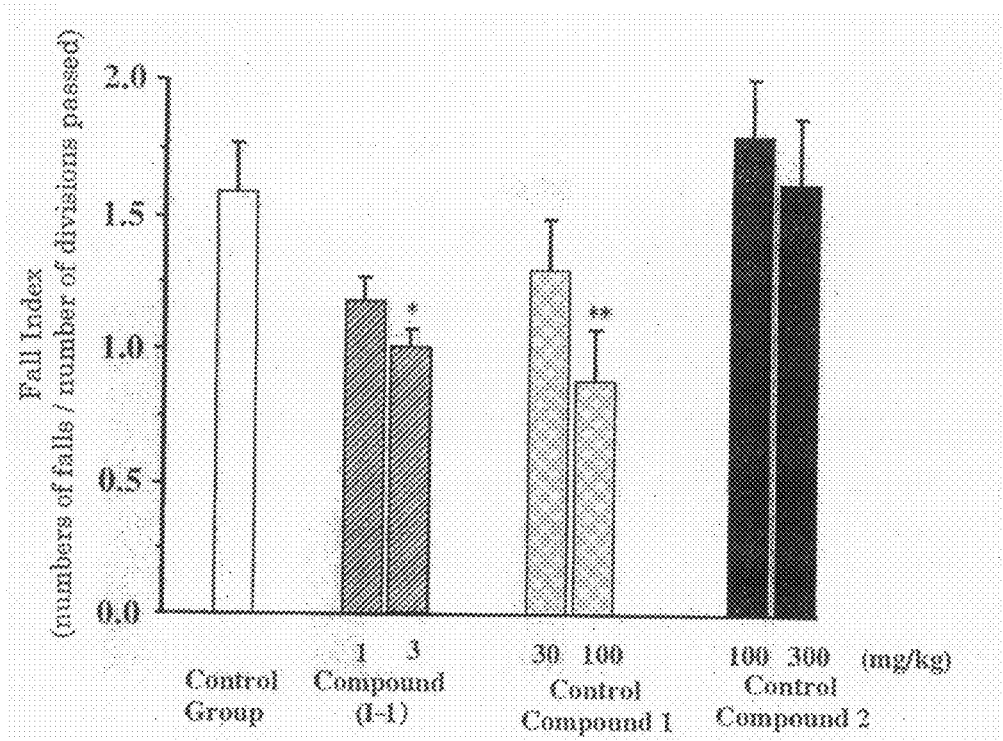
FIG. 1 shows an effect of Compound (I-1) for improving ataxia (equilibrium disturbance) in rolling mouse Nagoya.

In the present specification, the term "solvate" includes hydrate, solvate with an organic solvent and the like. The compound of the present invention may be coordinate with an arbitrary number of water molecules to give hydrate thereof. Monohydrate or trihydrate is preferable. A suspension of trihydrate in water is easy to handle for mass production because sedimentation rate of trihydrate particles is low. Therefore, trihydrate particularly preferable.

The compounds of the present invention include pharmaceutically acceptable salts of each compound. Exemplified are salts with an alkaline metal such as lithium, sodium, potassium or the like, salts with alkaline earth metals such as magnesium, calcium and the like, salts with ammonium, salts with an organic base, salts with an amino acid, salts with a mineral acid such as hydrochloric acid, hydrobromic acid, phosphoric acid, sulfuric acid or the like, and salts with an organic acid such as acetic acid, citric acid, maleic acid, fumaric acid, benzenesulfonic acid, p-toluenesulfonic acid or the like. These salts can be formed by usual manners.

The compounds of the present invention are not limited to a specific isomer and include all of formable isomers and racemates.

The compounds of the present invention can be produced by known methods described in Patent Literature 8, Patent Literature 9 and the like. Thus-obtained compounds can be changed to a salt or solvate such as hydrate thereof by usual manners.

The compounds of the present invention have a remarkable effect for improving ataxia (especially, motor ataxia caused by coordination disturbance and equilibrium disturbance) as mentioned below in Experimental Example. Because the compounds of the present invention have improved brain penetration rather than TRH or other TRH derivatives, the small amount of the compounds can show the certain drug efficacy. Moreover, although TRH and other TRH derivatives are easily metabolized in the brain, as the compounds of the present invention have the excellent intracerebral stability. Therefore, the compounds of the present invention are expected to show continuous drug efficacy. As a result, a dosage schedule is easily planned, and dose and frequency of dosage can be decreased. Therefore, the compounds of the present invention can be a preferable drug in consideration of patient's QOL.

These features mentioned above depends on the compounds of the present invention themselves. Patent Literature 8 discloses similar compounds to the compounds of the present invention. The compounds of the present invention, however, show higher effect for improving ataxia in comparison with the compounds in Patent Literature 8.

The compounds of the present invention have activities for treating or improving all of diseases and symptoms which are classifiable into spinocerebellar ataxia or multiple system atrophy. Examples of the diseases are hereditary olivo-pontocerebellar atrophy, hereditary cerebellar cortical atrophy, Friedreich ataxia, Machado-Joseph diseases, Ramsay Hunt syndrome, hereditary dentatorubral-pallidoluysian atrophy, hereditary spastic paraplegia, olivo-ponto-cerebellar atrophy, Shy-Drager syndrome, cortical cerebellar atrophy, striatonigral degeneration, Marinesco-Sjogren symdrome, alcoholic cortical cerebellar atrophy, paraneoplasic cerebellar atrophy associated with malignant tumor, toxic cerebellar atrophy caused by toxic substances, cerebellar atrophy associated with endocrine disturbance and the like. Examples of the symptoms are ataxia such as motor ataxia, trunk ataxia, limb ataxia and the like, autonomic disturbance such as orthostatic hypotension, dysuria, hypohidrosis, sleep apnea, orthostatic syncope and the like, stiffness of lower extremity, ocular nystagmus, oculomotor nerve disorder, pyramidal tract dysfunction, extrapyramidal symptom (postural adjustment dysfunction, muscular rigidity, akinesia, tremulus), dysphagia, lingual atrophy, posterior funiculus symptom, muscle atrophy, muscle weakness, deep hyperreflexia, sensory disturbance, scoliosis, kyphoscoliosis, foot deformans, anarthria, dementia, manic state, decreased motivation for rehabilitation and the like.

The compounds of the present invention are markedly effective for improvement of ataxia and equilibrium disturbance.

The term "ataxia" includes spinal ataxia, labyrinthine ataxia, cerebral ataxia and cerebellar ataxia. The compounds of the present invention are markedly effective for cerebellar ataxia (for example, motor ataxia caused by coordination disturbance and equilibrium disturbance).

A compound of the present invention can be administered to a human for treating or improving the above-mentioned diseases and symptoms by oral administration form such as powders, granules, tablets, capsules, pills, solutions and the like or parenteral administration form such as injections, suppositories, endermic agents, vapor and the like. A pharmaceutical composition can be prepared by mixing an effective dose of a compound of the present invention with various additives suitable for the administration form, such as excipients, binders, moistening agents, disintegrators, lubricants and the like, if needed. When the composition is an injection, a compound together with a suitable carrier can be sterilized to give a pharmaceutical composition. Oral administration by pills, capsules, buccals, jelly tablets, solutions and the like are preferable.

Although the dosage of a compound of the present invention should be determined in consideration of the degree of the diseases, the administration route, patient's age and body weight etc., an usual oral dosage for an adult is 0.01 to 100 mg/day and preferable is 0.1 to 40 mg/day, and more preferable is 0.5 to 20 mg/day. For parenteral administration, although the dosage highly depends on administration routes, an usual dosage is 0.001 to 10 mg/day, preferable is 0.01 to 4 mg/day, and more preferable is 0.05 to 2 mg/day.

The present invention is further explained by the following Examples and Experiments, which are not intended to limit the scope of the present invention.

The abbreviations mentioned below are used in the Examples.
BOC: t-butoxycarbonyl
p-Ts: p-toluenesulfonyl
Me: methyl

EXAMPLE

Example 1

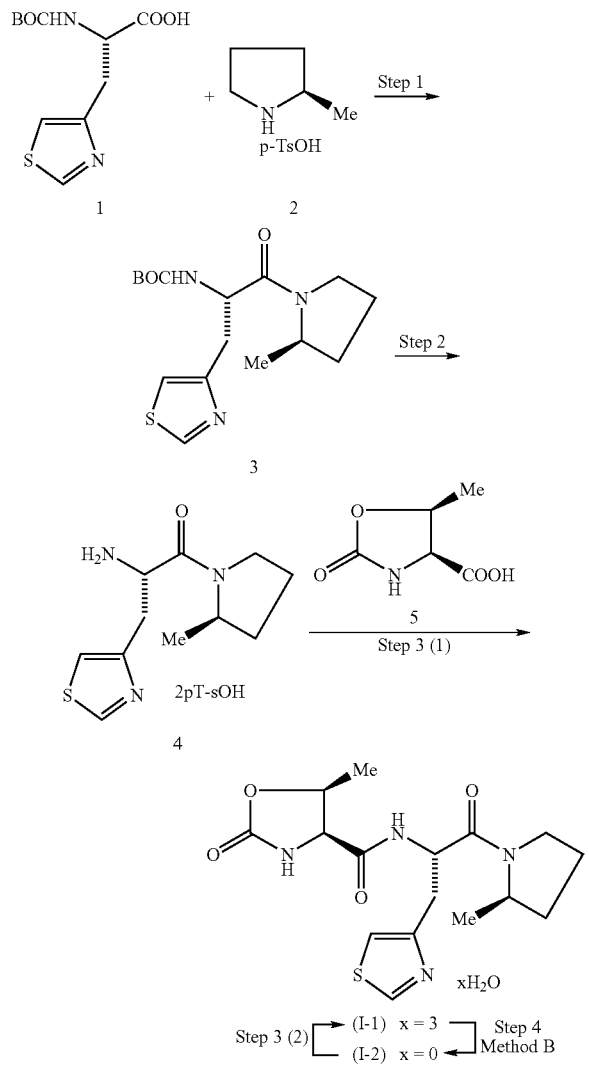

Step 1
1-N-[N-(tert-butoxycarbonyl)-3-(thiazol-4-yl)-L-alanyl]-(2R)-2-methylpyrrolidine (3)

N,N-dicyclohexylcarbodiimide (10.83 g, 52.5 mmol), N-hydroxybenzotriazole (2.03 g, 15 mmol) and triethylamine (7.7 ml, 55.2 mmol) were added to a solution (130 ml) of N-(tert-butoxycarbonyl)-3-(thiazol-4-yl)-L-alanine (1) (13.62 g, 50 mmol) obtained by the method described in literatures (J. Am. Chem. Soc. 73, 2935 (1951) and Chem. Pharm. Bull. 38, 103 (1950)) and 2(R)-2-methylpyrrolidine p-toluenesulfonic acid (2) (12.79 g, 50 mmol) obtained by the method described in a literature (Helv. Chim. Acta, 34, 2202 (1951)) in tetrahydrofuran. The mixture was stirred for 20 hours at room temperature. After the precipitates are filtered off, the obtained filtrate was concentrated under reduced pressure. Thus-obtained residue was dissolved in ethyl acetate (200 ml) and the solution were washed with an aqueous solution of sodium hydrogencarbonate and water, successively. The organic layers were dried over magnesium sulfate and concentrated under reduced pressure to give a title compound (3) (16.45 g, 100%) as oil.

NMR (CDCl$_3$): $\delta_H$ 8.76 and 8.75 (1H, each d, J=2.1 Hz, Thia-H-2), 7.08 (1H, d, J=2.1 Hz, thia-H-5), 5.45 (1H, m, NH), 3.45-3.64 (1H, m, Ala-C$\alpha$H), 4.14 and 3.81 (1H each m, Pyr-C$\alpha$H), 3.51 (1 H, m, pyr-NCH$_2$), 3.1-3.4 (3H, m, Pyr-CH$_2$ and Ala-CH$_2$), 1.39 (9H, s, BOC), 1.3-2.0 (4H, m, pyr-CH$_2$), 1.06 (3H, d, J=6 Hz, Pyr-Me)

Step 2
1-N-[3-(thiazol-4-yl)-L-alanyl]-(2R)-2-methylpyrrolidine di-p-toluenesulfonate (4)

Compound (3) (33.77 g, 99.48 mmol) and p-toluenesulfonic acid hydrate (37.85 g, 199 mmol) were dissolved in ethyl acetate (101 ml) and the solution was cooled with ice. To the mixture, 4 mol/L solution of hydrogen chloride-ethyl acetate (125 ml) was added, and the mixture was stirred for 2 hours 45 minutes. After the mixture was concentrated under reduced pressure, methanol was added to the residue. The mixture was concentrated. Methanol-toluene (1:1) was added to the residue and concentrated under reduced pressure to give crystalline residue. The residue was washed with acetone and filtered to give compound (4) as crystals (36 g, 62%). After the mother liquor was concentrated under reduced pressure, methanol and toluene were added to the residue and concentrated. Obtained crystalline residue was washed with acetone to give compound (4) (10.67 g, 18.4%).

mp 188-189° C.
$[\alpha]_D^{24}$ +2.2 (c, 1.0, MeOH)
IR(KBr)cm$^{-1}$: 3431, 3125, 3080, 2963, 1667, 1598, 1537, 1497, 1451, 1364, 1229, 1198, 1170, 1123, 1035, 1011.
NMR (CD$_3$OD): $\delta_H$ 9.04 and 9.03 (1H, each d, J=2.1 Hz, Thia-H-2), 7.70 (2H, m, aromatic H), 7.46 (1H, d, J=2.1 Hz, thia-H-5), 7.23 (2H, m, aromatic H), 4.49 and 4.46(1H, each d, J=6.9 Hz, Ala-C$\alpha$H), 4.14 and 3.75 (1H, each m, Pyr-C$\alpha$H), 3.51 (1H, m, pyr-NCH$_2$), 3.2-3.4 (3H, m, Pyr-CH$_2$ and Ala-CH$_2$), 2.36 (3H, s, aromatic Me), 1.3-2.0 (4 H, m, pyr-CH$_2$), 1.19 and 1.07 (3H, each d, J=6.3 Hz, Pyr-Me)

Anal Calcd For C$_{11}$H$_{17}$N$_3$OS 2C$_7$H$_8$O$_3$S Calculated: C, 51.44%; H, 5.70%; N, 7.20%; S, 16.48%. Found: C, 51.36%, H, 5.69%; N, 7.23%; S, 16.31%.

Step 3
1-[N-[(4S,5S)-(5-methyl-2-oxooxazolidin-4-yl)carbonyl]-3-(thiazol-4-yl)-L-alanyl-(2R)-2-methylpyrrolidine trihydrate (I-1)

Step 3 (1)
Method A
(4S, 5S)-5-methyl-2-oxooxazolidin-4-yl carboxylic acid (5) (1.368 g, 9.43 mmol) obtained by the method described in literatures (J. Chem. Soc. 1950, 62; Tetrahedron 48; 2507 (1992) and Angew. Chem. 101, 1392 (1989)), Compound (4) (5 g, 8.56 mmol) and N-hydroxysuccinimide (217 mg, 1.89 mmol) were dissolved in N,N-dimethylformamide (10 ml), and tetrahydrofuran (65 ml) was added. After the mixture was cooled with ice in a cool bath, triethylamine (2 63 ml, 18.86 mmol) and N, N-dicyclohexylcarbodiimide (2.04 g, 9.89 mmol) were added with stirred and the mixture was stirred for additional 30 minutes. The cooling bath was removed and the mixture was stirred for 15 hours at room temperature. The precipitated were filtered off and the filtrate was concentrated under reduced pressure. Water (100 ml) was added to thus-obtained residue (9.95 g) and the mixture was stirred for 1.5 hours at room temperature. After insoluble substance was filtered off, the filtrate was concentrated until it was reduced to about half volume under reduced pressure. The small amount of insoluble substance was filtered off and the filtrate was concentrated until it was reduced to about 20 g under reduced pressure. After the mixture was allowed to stand in a refrigerator for 3 days, the precipitated crystals (2.98 g) were collected by filtration and washed with cold water. The filtrate was extracted twice with chloroform, dried over magnesium sulfate and concentrated under reduced pressure. Ethyl acetate (5 ml) was added to oil residue (1.05 g) and the mixture was stirred to give crystals (136 mg). The obtained crystals were combined and dissolved in purified water (45 ml) with heating. After the solution was allowed to cool to room temperature, the precipitated insoluble substance was filtered off. The filtrate was concentrated under reduced pressure and allowed to stand at room temperature overnight. The mixture was cooled with ice, and the crystals were collected by filtration to give Compound (I-1, 2.89 g, 80.3%).

mp 194-196° C.

$[\alpha]_D^{22}$ −2.0±0.4° (c, 1.008, $H_2O$), $[\alpha]_{365}$ +33.1±0.7° (c, 1.008, $H_2O$)

IR(Nujor) cm$^{-1}$: 3517, 3342, 3276, 3130, 3092, 3060, 1754, 1682, 1610, 1551, 1465, 1442, 1379, 1235, 1089.

NMR (CD$_3$OD): $\delta_H$ 897 and 8.96 (total 1H, d, J=2.1 Hz, Thia-H-2), 7.34 and 7.33 (total 1H, d, J=2.1 Hz, Thia-H-5), 5.18 and 5.04 (total 1H, each t, J=7.5 Hz, Ala-CαH), 4.92 (1H, dq, J=6.6 and 8.7 Hz, Oxa-H-5), 4.36 and 4.35 (total 1H, d, J=8.7 Hz, Oxa-H-4), 4.07 and 3.92 (total 1H, each m, Pyr-Cα-H), 3.78 (1H, m, Pyr-NCH$_2$), 3.42 (1H, m, Pyr-NCH$_2$), 3.22 (2H, m, Ala-CH$_2$), 1.5-2.0 (4H, m, Pyr-CH$_2$) 1.28 and 1.22 (total 3H, each d, J=6.6 Hz, Oxa-5-Me), 1.21 and 1.02 (total 3H, each d, J=6.6 Hz, Pyr-2-Me)

Anal. Calcd For $C_{16}H_{22}N_4O_4S$ $3H_2O$ Calculated: C, 45.00%; H, 6.71%; N, 13.33%; S, 7.63%. Found: C, 45.49%; H, 6.60%; N, 13.58%, S, 7.88%.

Step 3 (2)

Method B

After Compound (I-2) (410 g, 1.119 mmol) was dissolved in purified water (6.3 L) with heating, the solution was concentrated until the total weight of the mixture was reduced to 1370 g under reduced pressure. The concentrated solution was allowed to stand at room temperature overnight. The solution was cooled with ice for 1 hour and filtered to give the precipitated crystals. The obtained crystals were washed with cold water to give Compound (I-1) (448 g, 95.2%) as colorless crystals. Mother liquor was mixed with purified water (300 mL) with heating and the solution was concentrated to 55 g under reduced pressure. After the concentrated solution was allowed to stand at room temperature overnight, the solution was filtered to give the precipitated crystals (I-1, 16.3 g, 3.5%, total amount 464.3 g, 98.7%).

mp 194-196° C.

$[\alpha]_D^{22}$ −0.9±0.4° (c, 1.007, $H_2O$), $[\alpha]_{365}$ +35.4±0.8° (c, 1.007, $H_2O$)

IR(Nujor)cm$^{-1}$: 3511, 3348, 3276, 3130, 3093, 3060, 1755, 1739, 1682, 1611, 1551, 1465, 1442, 1379, 1235, 1089.

Anal Calcd For: $C_{16}H_{22}N_4O_4S$ $3H_2O$ Calculated: C, 45.00%; H, 6.71%; N, 13.33%; S, 7.63%. Found: C, 45.56%; H, 6.66%; N, 13.43%, S, 7.69%.

Step 4

1-[N-[(4S,5S)-(5-methyl-2-oxooxazolidin-4-yl)carbonyl]-3-(thiazol-4-yl)-L-alanyl-(2R)-2-methylpyrrolidine (I-2)

Method A

After 1-[N-[(4S,5S)-(5-methyl-2-oxooxazolidin-4-yl)carbonyl]-3-(thiazol-4-yl)-L-alanyl-(2R)-2-methylpyrrolidine monohydrate (4.77 g) obtained by the method described in Patent Literature 8 was crushed in a mortar, it was dried under reduced pressure (66.5 Pa) at 100° C. for 15 hours to give 4.54 g of Compound (I-2).

mp 194.5-196.5° C.

$[\alpha]_D^{25}$ −2.1±0.4° (c, 1004, $H_2O$), $[\alpha]_{365}$ +36.8±0.8° (c, 1004, $H_2O$)

Water measurement (Karl Fischer method): 0.27%

IR(Nujor)cm$^{-1}$: 3276, 3180, 3104, 1766, 1654, 1626, 1548, 1517, 1457; 1380, 1235, 1102, 979.

NMR (CD$_3$OD): $\delta_H$ 8.97 and 8.96 (total 1H, d, J 2.1 Hz, Thia-H-2), 7.34 and 7.33 (total 1 H, d, J 2.1 Hz, Thia-H-5), 5.19 and 5.04 (total 1H, each t, J 7.5 Hz, Ala-CαH), 4.92 (1H, dq, J 6.6 and 8.7 Hz, Oxa-H-5), 4.36 and 4.35 (total 1H, d, J 8.7 Hz, Oxa-H-4), 4.07 and 3.92 (total 1H, each m, Pyr-Cα-H), 3.78 (1H, m, Pyr-NCH$_2$), 3.42 (1 H, m, Pyr-NCH$_2$), 3.22 (2H, m, Ala-CH$_2$), 1.5-2.0 (4H, m, Pyr-CH$_2$), 1.28 and 1.22 (total 3H, each d, J 6.6 Hz, Oxa-5-Me), 1.21 and 1.02 (total 3H, each d, J 6.6 Hz, Pyr-2-Me).

Anal Calcd For: $C_{16}H_{22}N_4O_4S$ Calculated: C, 52.44%; H, 6.05%; N, 15.29%; S, 8.75%. Found: C, 52.24%; H, 5.98%; N, 15.27%, S, 8.57%.

Method B

After Compound (I-1) (17.89 g, 47:3 mmol) was crushed in a mortar, it was dried under reduced pressure (66.5 Pa) at 100° C. for 14 hours to give Compound (I-2, 17.31 g).

mp 193-194° C.

$[\alpha]_D^{25}$ −1.9±0.4° (c, 1.002, $H_2O$), $[\alpha]_{365}$ +37.2±0.8° (c; 1.002, $H_2O$)

Water measurement (Karl Fischer method): 0.22%

IR(Nujor)cm$^{-1}$: 3273, 3180, 3111, 1765, 1685, 1653, 1626, 1549, 1516, 1456, 1346, 1331, 1277, 1240, 1097, 980.

Anal Calcd For $C_{16}H_{22}N_4O_4S$ Calculated: C, 52.44%; H, 6.05%; N, 15.29%; S, 8.75%. Found: C, 52.19%; H, 5.98%; N, 15.42%, S, 8.74%.

Experiment 1 Effect of improving ataxia on Rolling Mouse Nagoya

Rolling Mouse Nagoya, a hereditary ataxia mouse, is known as a model mouse for spinocerebellar ataxia and has been reported in many papers (E. Kurihara, N. Fukuda, S. Narumi, T. Matsuo, S. Saji, and Y. Nagawa, Jpn. Pharmacol., Ther., 13, 49-56 (1985), Y. Mano, K. Matsui, E. Toyoshima, and K. Ando, Acta. Neurol. Scand., 73, 352-358 (1986), K. Kinoshita, T. Fujitsuka, M. Yamamura, and Y. Matsuoka, Eur. J. Pharmacol., 274, 65-72 (1995), K. Kinoshita, T. Fukushima, Y, Kodama, J. Sugihara, M. Yamamura, and Y. Matsuoka, Biol. Pharm. Bull., 20, 36-39 (1997)).

Effect of Compound (I-1) for ataxia of Rolling Mouse Nagoya was investigated. The following compounds in Patent Literature 1 and Non-Patent Literature 1 were used as Control Compounds 1 and 2.

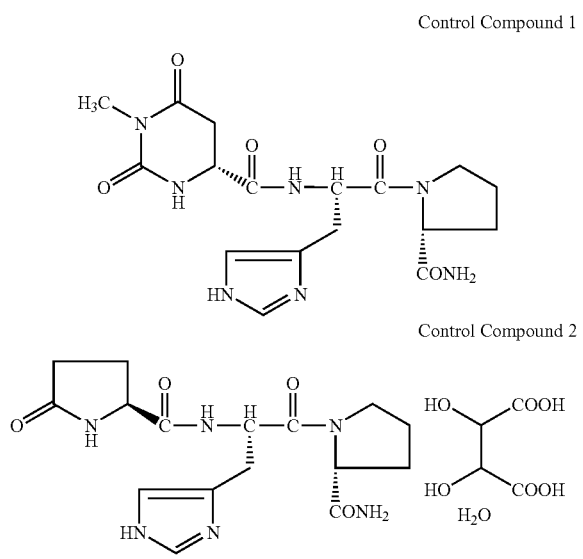

Control Compound 1

Control Compound 2

An effect on improvement of ataxia was evaluated with a fall index by an open-field method. Mice were left in the center of an open-field (circle open-field, 75 cm in a diameter, 25 divisions). Number of divisions passed and numbers of falls for 5 minutes were counted, and a fall index (numbers of falls/number of divisions passed) was calculated.

Each of the compounds was dissolved in a physiological saline on the day of the experiment. Each compound was orally administered to mice using a sonde for oral administration at the following dosage; Compound (I-1): 1 mg/kg and 3 mg/kg, Control Compound 1: 30 mg/kg and 100 mg/kg, Control Compound 2: 100 mg/kg and 300 mg/kg. Physiological saline alone was administered to mice as a control group. Volume for oral administration was 0.2 mL per 20 g body weight of a mouse.

Effect on improvement of ataxia for each mouse was evaluated 1 hour after administration by the open-field method. Sample numbers were 5 or more in every group.

The results are shown in FIG. 1 (*: $p<0.05$, **: $p<0.01$). Compound (I-1) shows superior effect on improvement of ataxia at 3 mg/kg to Control Compounds. Control Compound 1 shows superior effect of improving ataxia to that in a control group only at 100 mg/kg dosage. Control Compound 2 does not show the improvement effect even at 300 mg/kg dosage.

The above-mentioned results show Compound (I-1) have 30 times or more excellent effect of improving ataxia than Control Compound 1 and 100 times or more than Control Compound 2.

Although the compounds of the present invention have higher BA than control compounds as described in Patent Literature 10, these show much higher effect of improving ataxia than control compounds. It is not considered that such excellent effect depends on only BA, and the compounds of the present invention have the superior effect of improvement on ataxia.

Experiment 2 Effect of improving ataxia on cerebellum-injured rat by administration of Ara-C Ara-C (60 mg/kg, Nippon Shinyaku) was subcutaneously administered to Sprauge-Dawley rats (CLEA Japan, Inc) of 2 days old and 3 days old, and the effects of improving ataxia on Compound (I-1), Control Compound 1 and Control Compound 2 at 4 weeks old were investigated.

The effect of improving on ataxia was evaluated with a fall index by an open-field method. Rats were left in the center of an open-filed (circle open-filed, 75 cm in a diameter, 25 divisions), number of divisions passed and numbers of falls for 3 minutes were counted, and a fall index (numbers of falls/number of divisions passed) was calculated.

Each of the compounds was dissolved in a physiological saline on the day of administration. Each compound was orally administered to rats using a sonde for oral administration at the following dosage; Compound (I-1): 0.1 mg/kg, 0.3 mg/kg, 1 mg/kg and 3 mg/kg, Control Compound 1: 30 mg/kg and 100 mg/kg, Control Compound 2: 100 mg/kg and 300 mg/kg. Physiological saline alone was administered to rats as a control group. The compounds were repetitively orally administered one a day for seven days and the effect was investigated 24 hours after the final administration. Volume for oral administration was 0.1 mL per 100 g body weight of a rat. Sample numbers were 5 or more in every group.

Figure 2:
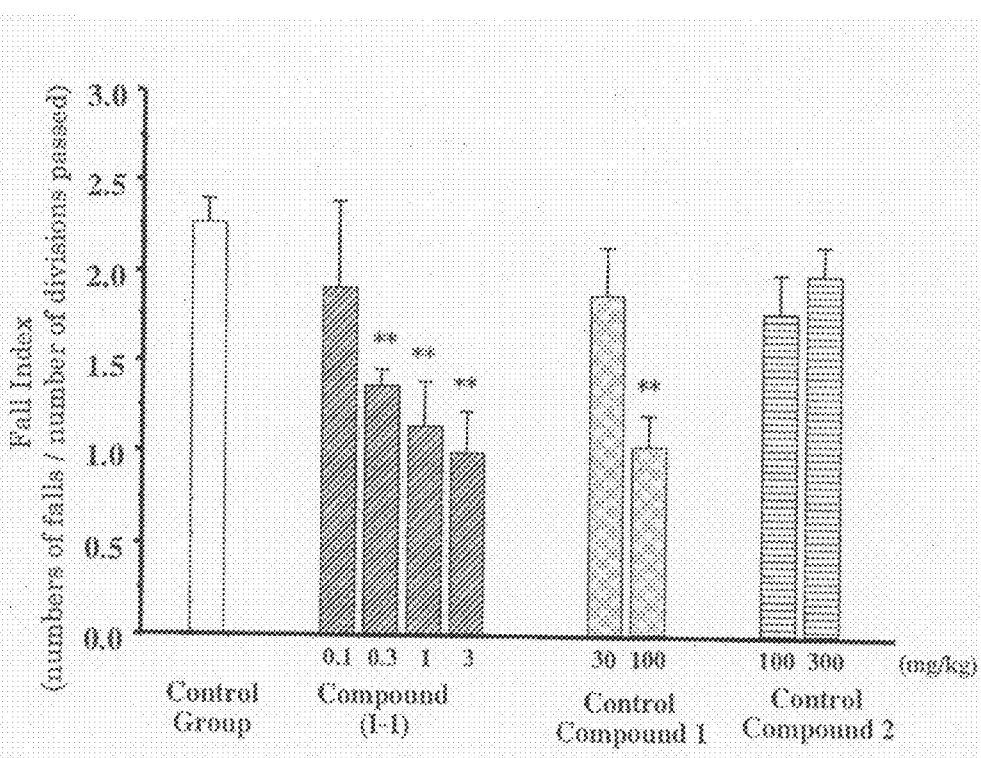
FIG. 2 shows an effect of Compound (I-1) for improving ataxia (equilibrium disturbance) in cerebellum-damaged rat induced by Ara-C.

The results are shown in FIG. 2 (**: $p<0.01$). Compound (I-1) shows superior effect on improvement of ataxia to Control Compounds at 0.3 mg/kg or more. Control Compound 1 shows superior effect on improvement of ataxia in comparison of a control group only at 100 mg/kg dosage. Control Compound 2 does not show the improvement effect even at 300 mg/kg dosage.

As shown in the above-mentioned results, Control Compound 1 has the same level efficacy as 1/300 dosage of Compound (I-1) and Control Compound 2 has the same level efficacy as 1/1000 or less dosage of Compound (I-1). Therefore, the results show Compound (I-1) has the excellent effect of improving ataxia.

Similar to Experiment 1, the results show that the remarkable effect of improving ataxia of the compounds of the present invention can not depend only on BA.

Experiment 3 Effect of improving ataxia on Rolling Mouse Nagoya

Effects of the compounds described in Patent Literature 8 (I-3: R=CN, I-1: R=CONH$_2$) and Control Compound 2 on ataxia on Rolling Mouse Nagoya were investigated.

The effect on ataxia was evaluated with a fall index by an open-field method. Mice were left in the center of an open-field (square open-field, 100 cm×100 cm, divided into 25 squares of 20 cm×20 cm), number of squares passed and numbers of falls for 10 minutes were counted, and a fall index (numbers of falls/number of squares passed) was calculated.

Each of the compounds was dissolved in a physiological saline on the day of the experiment. Each compound was orally administered to mice using a sonde for oral administration at the following dosage; Compounds (I-3) and (I-4): 10 mg/kg, Control Compound 2: 100 mg/kg. Volume for oral administration was 0.2 mL per 20 g body weight of a mouse.

Each of the test compound was orally administered just after a fall index of each mouse in the open-field was calculated. A fall index was calculated again 1 hour after administration and the effect of improving ataxia was evaluated. Sample numbers were 5 or more in every group.

Figure 3:
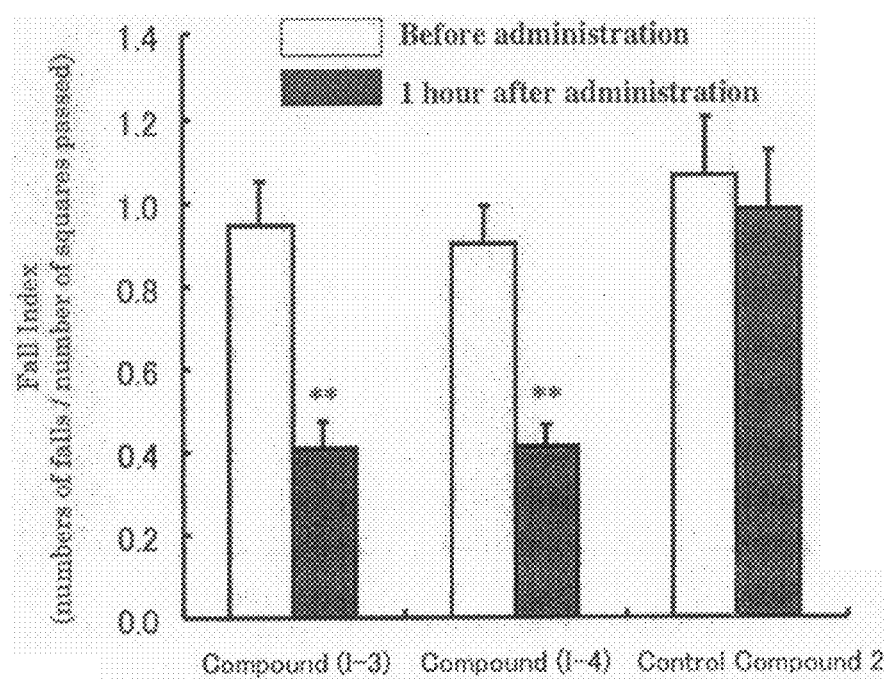
FIG. 3 shows effects of Compounds (I-3) and (I-4) for improving ataxia (equilibrium disturbance) in rolling mouse Nagoya.

The results are shown in FIG. 3 (*: $p<0.05$, **: $p<0.01$). Compounds (I-3) and (I-4) show excellent effect of improving ataxia by oral administration and Control Compound 2 shows weak improvement effect.

These results show that Compounds (I-3) and (I-4) have remarkable effect of improving ataxia.

Formulation Example 1

Granules are prepared using the following ingredients.

| | |
|---|---|
| Compound (I) | 10 mg |
| Lactose | 700 mg |
| Corn Starch | 274 mg |
| HPC-L | 16 mg |
| | 1000 mg |

Compound (I) and lactose are made pass through a 60 mesh sieve. Corn starch is made pass through a 120 mesh sieve. They are mixed by a V-type mixer. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a vibrating sieve (12/60 mesh) to yield the granules.

Formulation Example 2

Powders for filling capsules are prepared using the following ingredients.

| | |
|---|---|
| Compound (I) | 10 mg |
| Lactose | 90 mg |
| Corn Starch | 42 mg |
| HPC-L | 3 mg |
| | 150 mg |

Compound (I) and lactose are made pass through a 60 mesh sieve. Corn starch is made pass through a 120 mesh sieve. After they are mixed, an aqueous solution of HPC-L is added to the mixture and the resulting mixture is kneaded, granulated, and dried. Size of the dried granules thus obtained is regulated, 150 mg of them are filled into a No. 4 hard gelatin capsule.

Formulation Example 3

Tablets are prepared using the following ingredients.

| | |
|---|---|
| Compound (I) | 10 mg |
| Lactose | 90 mg |
| Microcrystal cellulose | 30 mg |
| CMC-Na | 15 mg |
| Magnesium stearate | 5 mg |
| | 150 mg |

Compound (I), lactose, microcrystal cellulose, and CMC-Na (carboxymethylcellulose sodium salt) are made pass through a 60 mesh sieve and then mixed. The resulting mixture is mixed with magnesium stearate to obtain mixed powders for a tablet formulation. The mixed powders are compressed to yield tablets of 150 mg.

Industrial Applicability

The compounds of the present invention can be an useful medicament for treating spinocerebellar ataxia or multiple system atrophy, or for improving ataxia or equilibrium disturbance.

The invention claimed is:

1. A method for treating spinocerebellar ataxia or multiple system atrophy, comprising administering a therapeutically effective amount of a compound of the formula (I):

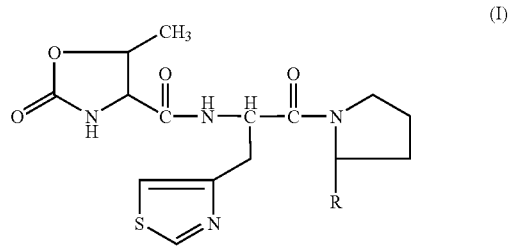

wherein R is methyl, or a pharmaceutically acceptable salt or a hydrate thereof, to a mammal in need thereof.

2. A method for treating spinocerebellar ataxia, comprising administering a therapeutically effective amount of a compound of the formula (I):

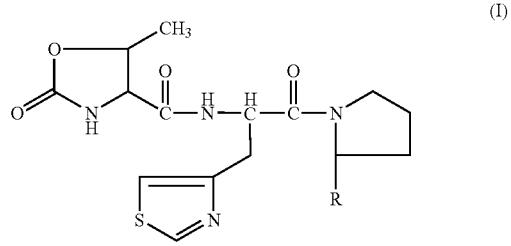

wherein R is methyl, or a pharmaceutically acceptable salt or a hydrate thereof, to a mammal in need thereof.

3. A method for improving ataxia caused by spinocerebellar ataxia or multiple system atrophy, comprising administering a composition comprising a therapeutically effective amount of a compound of the formula (I):

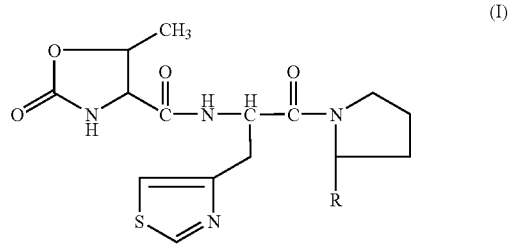

wherein R is methyl, or a pharmaceutically acceptable salt or a hydrate thereof as an active ingredient, to a mammal in need thereof.

4. A method for improving equilibrium disturbance caused by spinocerebellar ataxia or multiple system atrophy, comprising administering a composition comprising a therapeutically effective amount of a compound of the formula (I):

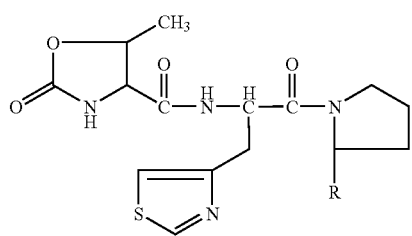

(I)

wherein R is methyl, or a pharmaceutically acceptable salt or a hydrate thereof as an active ingredient, to a mammal in need thereof.

5. The method of claim 1 or 2, wherein spinocerebellar ataxia or multiple system atrophy is olivo-ponto-cerebellar atrophy or striato-nigral degeneration.

6. The method of any one of claims 1-4, wherein the compound of the formula (I) is a monohydrate or trihydrate of the compound.

7. The method of claim 5, wherein the compound of the formula (I) is a monohydrate or trihydrate of the compound.

* * * * *

UNITED STATES PATENT AND TRADEMARK OFFICE
CERTIFICATE OF CORRECTION

| | | |
|---|---|---|
| PATENT NO. | : 8,071,633 B2 | Page 1 of 1 |
| APPLICATION NO. | : 11/662182 | |
| DATED | : December 6, 2011 | |
| INVENTOR(S) | : Takayoshi Yoshikawa et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 941 days.

Signed and Sealed this

Fourteenth Day of February, 2012

David J. Kappos
*Director of the United States Patent and Trademark Office*